US010138451B2

(12) United States Patent
Reid et al.

(10) Patent No.: US 10,138,451 B2
(45) Date of Patent: Nov. 27, 2018

(54) CELL CULTURE DISH SUPPORTING SIMULTANEOUSLY JUXTAPOSED AND SEPARATED CULTURES

(71) Applicants: Christopher B. Reid, Los Angeles, CA (US); Keith Norris, Marina Del Rey, CA (US); Taehoon Cho, Los Angeles, CA (US); Victor Chaban, Los Angeles, CA (US)

(72) Inventors: Christopher B. Reid, Los Angeles, CA (US); Keith Norris, Marina Del Rey, CA (US); Taehoon Cho, Los Angeles, CA (US); Victor Chaban, Los Angeles, CA (US)

(*) Notice: Subject to any disclaimer, the term of this patent is extended or adjusted under 35 U.S.C. 154(b) by 12 days.

(21) Appl. No.: 14/764,195

(22) PCT Filed: Jan. 29, 2014

(86) PCT No.: PCT/US2014/013473
§ 371 (c)(1),
(2) Date: Jul. 29, 2015

(87) PCT Pub. No.: WO2014/120702
PCT Pub. Date: Aug. 7, 2014

(65) Prior Publication Data
US 2016/0002585 A1    Jan. 7, 2016

Related U.S. Application Data

(60) Provisional application No. 61/849,589, filed on Jan. 30, 2013.

(51) Int. Cl.
*C12M 1/22* (2006.01)
*C12M 1/32* (2006.01)
(Continued)

(52) U.S. Cl.
CPC ............ *C12M 23/12* (2013.01); *C12M 23/10* (2013.01); *C12M 23/22* (2013.01); *C12M 23/34* (2013.01); *C12M 25/06* (2013.01)

(58) Field of Classification Search
CPC ...... C12M 23/10; C12M 23/12; C12M 23/22; C12M 23/34; C12M 25/06
(Continued)

(56) References Cited

U.S. PATENT DOCUMENTS 3,097,070 A * 7/1963 Aldrich ................. B01L 3/508
                                                            215/12.2
3,660,243 A    5/1972 Young
(Continued)

FOREIGN PATENT DOCUMENTS

WO    2014120702 A1    8/2014

OTHER PUBLICATIONS

U.S. Appl. No. 61/849,589, filed Aug. 7, 2014, Reid et al.

*Primary Examiner* — Nathan A Bowers
*Assistant Examiner* — Lydia Edwards

(57) ABSTRACT

The present invention relates to a novel culturing apparatus (assembly) which can be termed a cell culture dish. More particularly, the present invention is a "combined cell culture dish" or "dish-in-dish" apparatus comprising at least one smaller cell culture dish fixedly positioned within a larger cell culture dish, and the number of such fixated cell culture dishes can include a multiple number of fixated cell culture dishes within one another, either concentric or eccentric, in any number of geometric shapes, and without limitation to the number of petri dishes included. An alternate embodiment of this invention can include a plurality of cell culture dishes juxtaposed side-by-side having common interior well walls, and the well walls may or may not be different in height depending on the application.

10 Claims, 2 Drawing Sheets

(51) Int. Cl.
*C12M 1/00* (2006.01)
*C12M 1/107* (2006.01)
*C12M 1/12* (2006.01)

(58) Field of Classification Search
USPC .................................................. 435/305.2
See application file for complete search history.

(56) References Cited

U.S. PATENT DOCUMENTS

| | | | |
|---|---|---|---|
| 4,160,700 A | | 7/1979 | Boomus et al. |
| 4,668,633 A | * | 5/1987 | Walton ................... C12M 23/10 435/305.2 |
| 4,675,298 A | | 6/1987 | Brusewitz |
| 5,650,323 A | * | 7/1997 | Root ..................... B01L 3/5085 210/238 |
| 6,156,566 A | * | 12/2000 | Bryant ................... C12M 23/10 435/2 |
| 2004/0214313 A1 | * | 10/2004 | Zhang ................... C12M 23/10 435/288.4 |
| 2009/0068696 A1 | * | 3/2009 | Frimodt-Moller ..... C12Q 1/045 435/19 |
| 2011/0172128 A1 | * | 7/2011 | Davies ................. B01L 3/5085 506/33 |

* cited by examiner

CELL CULTURE DISH SUPPORTING SIMULTANEOUSLY JUXTAPOSED AND SEPARATED CULTURES

BACKGROUND OF THE INVENTION

The present invention relates to a novel culturing apparatus (assembly) which can be termed a cell culture dish. More particularly, the present invention is a "combined cell culture dish" or "dish-in-dish" apparatus comprising at least one smaller cell culture dish fixedly positioned within a larger cell culture dish, and the number of such fixated cell culture dishes can include a multiple number of fixated cell culture dishes within one another, either concentric or eccentric, in any number of geometric shapes, and without limitation to the number of petri dishes included. An alternate embodiment of this invention can include a plurality of cell culture dishes juxtaposed side-by-side having common interior well walls, and the well walls may or may not be different in height depending on the application. The combined cell culture dish differs from the prior art because the walls of said combined petri dishes may be of different heights and made from any combination of transparent and non-transparent materials that will allow juxtaposing and different cultures to grow simultaneously. Such separate but juxtaposing culture growth can then be studied to determine whether certain cultures gown separately and in close proximity influence each other in certain ways. The combined cell culture dish of the present invention may or may not be fitted with single or multiple covers and may or may not be stacked.

Examples of prior petri dishes may be found in the following U.S. Pat. No. 4,675,298 (Brusewitz, Gerhard), U.S. Pat. No. 4,160,700 (Boomus, Mary), and U.S. Pat. No. 3,660,243 (Young, Cecil).

SUMMARY OF THE INVENTION

The present invention is directed to a novel cell culture dish having a multi-chambered construction which facilitates juxtaposition of different physically separated cultures. Said novel multi-chambered cell culture dish will permit co-culturing of any two or more separate cultures, whether those cultures are species related or not.

In general, the cell culture dish of the present invention comprises two or more dishes which create a central compartment and one or more peripheral compartments which surround the central compartment. Said central and peripheral compartments may take the form of any shape, including, but not limited to cylindrical, square, pentagonal, or hexagonal. The material used to construct said petri dish may include, but may not be limited to, any non media-permeable form of glass, plastic or metal or combination thereof, which will sustain culture growth and permit observation and recording of said culture growth, including, but not limited to, the recording of signal transduction. Separated areas created by utilizing the central compartment and one or more peripheral compartments may be geometrically concentric or eccentric.

The petri dish of the present invention may comprise one or more dishes within a dish or may be constructed of a single dish with a flat well bottom having one or more sets of walls that extend from said well bottom forming one or more separate enclosures having the same geometric shape or a variety of geometric shapes. The wall or walls are constructed to ensure physical isolation of two or more sets of cells from one another to prevent physical contact between the separated cells or movement of chemical factors originating in the media or within the cells. The separate wells may or may not be numbered to enhance the identification of certain cell cultures.

A preferred embodiment of this invention is depicted in FIG. 1 below.

The petri dish described above can be sterilized using either wet or dry heat. However, the petri dish may be a single use device as well. The outer wall of the multi-chambered petri dish can be sized appropriately to fit high-performance incubation and perfusion chambers for live cell imaging and to withstand temperatures ranging from 5 degrees below Celsius to 50 degrees above Celsius. However, the multi-chambered petri dishes of this invention may also withstand a host of temperatures outside the previously stated range.

One object of the present invention is to provide a multi-chambered cell or tissue culture dish suitable for assessing cell communication that is not prohibited by intervention of the chamber walls.

Another object of this invention is to provide a cell or tissue culture dish having a plurality of separate wells which permit communication between cells or tissues situated within said wells of signals or communication which might emanate from said cells or tissues.

Still another object of this invention is to provide a multi-chambered cell or tissue culture dish with a transparent and flat bottom to enable convenient and accurate viewing and analysis of the contents of each separate chamber.

A further object of this invention is to provide a multi-chambered cell or tissue culture dish which can be made from a number of transparent materials, including, but not limited to, glass, acrylic polymers, fluorinated ethylene propylene, ultra high molecular weight polyethylene, polycarbonate, polystyrene, or any amorphous high-performance polymer.

Yet another object of this invention is to provide a multi-chambered cell or tissue culture dish manufactured with well walls having different heights and defining an outer "surround" cell culture and one or more inner "center" cell cultures to enable contained cell or tissue communication within the well spaces. Such communication would include, but would not be limited to, putative nociceptive cell signaling in physically disconnected but proximal cell populations, including cell-to-cell communications which are taking place after eliminating the availability of any potential pathways for neural or diffusible factor mediated cell-cell communication.

DETAILED DESCRIPTION OF FIGURES

Figure 1:
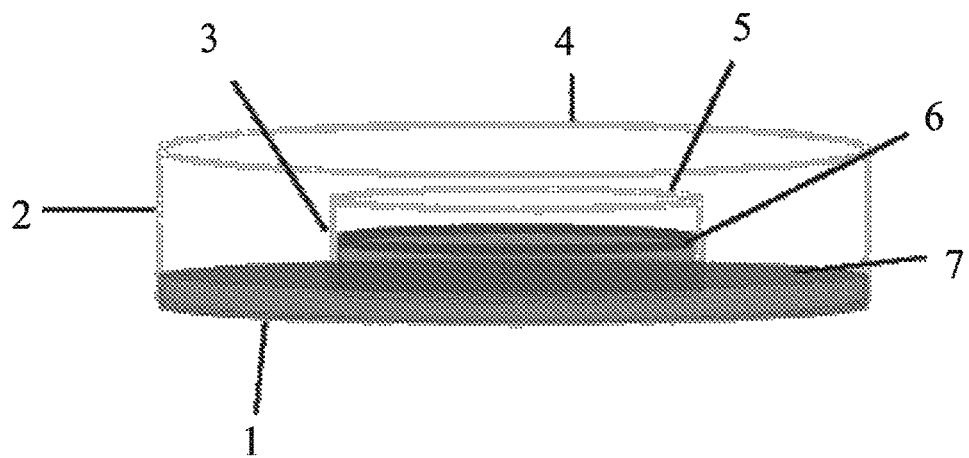
FIG. 1 is a front view of a two well cell or tissue culture dish constructed according to this invention, containing different cell or tissue cultures within each separate well.

The multi-chambered cell or tissue culture dish shown in FIG. 1 is composed of a common base 1 made of the same transparent chemical resistant material. In the present embodiment, two wells are formed as depicted, the center well being defined by well wall 3 and the surround well being defined by well wall 2 which is dimensionally higher, as can be determined by measuring from the base 1 to the surround cell wall rim 4, than is well wall 3 which is measured from the base 1 to the center cell wall rim 5. It is understood that a greater number of center wells may be provided depending on the application having differing cell wall heights. FIG. 1 also depicts a cell or tissue culture 7, situated in the surround well, which is defined dimensionally by the base 1, the surround well wall 2 and the center well wall 3. FIG. 1 also depicts a cell or tissue culture 6, situated in the center well as defined dimensionally by the base 1, and the center well wall 3.

Figure 2:
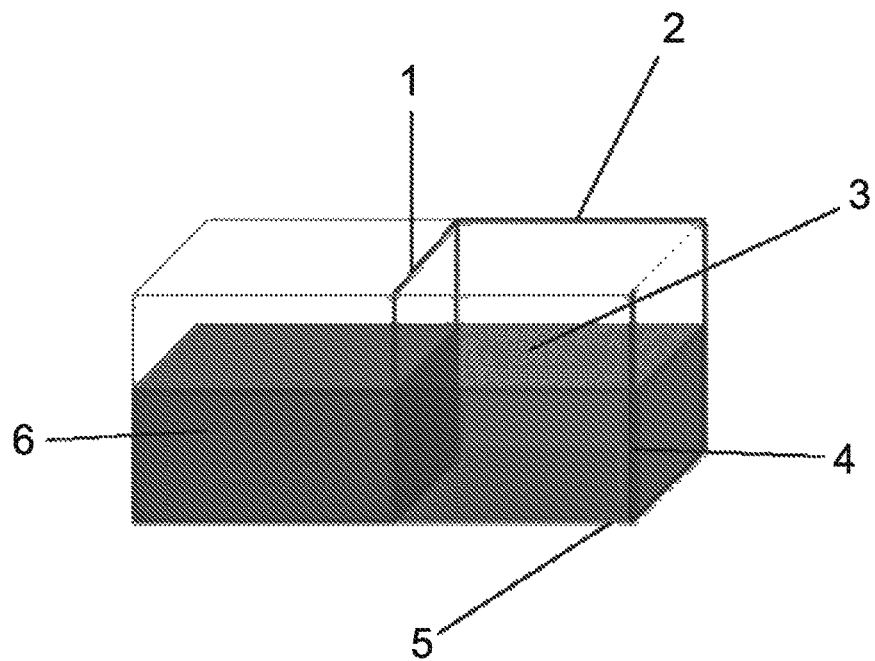
FIG. 2 is a front view of a two well cell or tissue culture dish constructed according to this invention with the wells positioned side-by-side.

The multi-chambered cell or tissue culture dish shown in FIG. 2 is composed of a common base 5 made of the same transparent chemical resistant material. In the present embodiment, two wells are formed as depicted, the left well being separated from the right well by well wall 1 and the right well being defined by well walls 1, 2, 3, and 4. It is understood that a greater number of wells than the two depicted may be juxtaposed together depending on the application. FIG. 2 also depicts a cell or tissue culture 6 situated in the left well.

Figure 3:
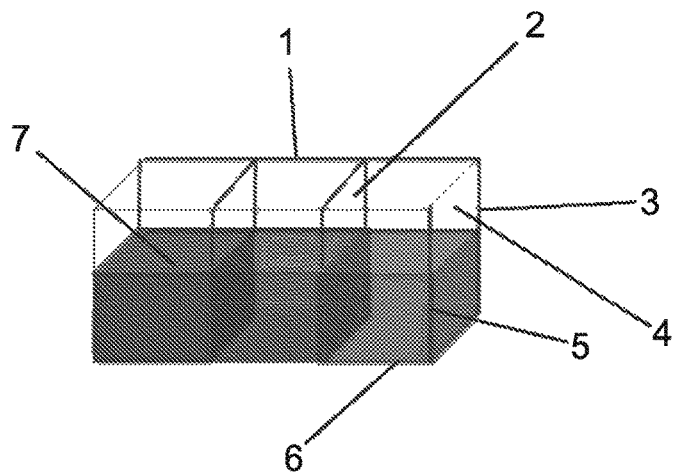
FIG. 3 is a front view of a three well cell or tissue culture dish constructed according to this invention with the wells positioned side-by-side.

The multi-chambered cell or tissue culture dish shown in FIG. 3 is composed of a common base 6 made of the same transparent chemical resistant material. In the present embodiment, three wells are formed as depicted, the right well being separated from the middle well by well wall 2 and the right well being defined by well walls 2, 3, 4, and 5. It is understood that a greater number of wells than the three depicted may be juxtaposed together depending on the application. FIG. 3 also depicts a cell or tissue culture 7 situated in the far left well.

Figure 4:
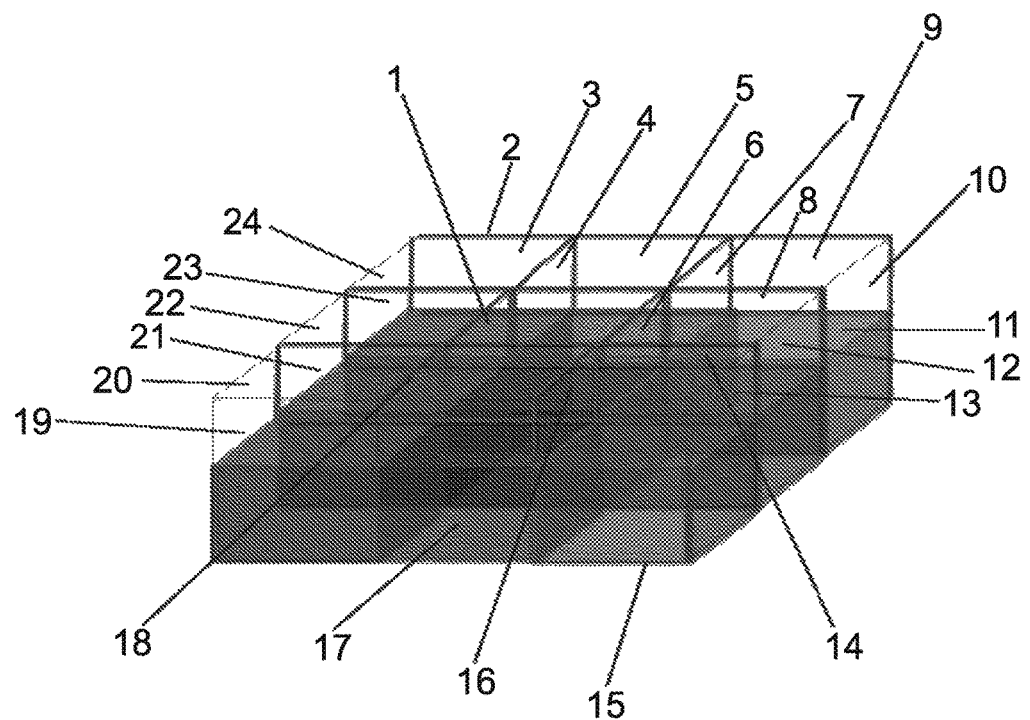
FIG. 4 is a front view of a nine well cell or tissue culture dish constructed according to this invention with the wells positioned side-by-side.

The multi-chambered cell or tissue culture dish shown in FIG. 4 is composed of a common base 15 made of the same transparent chemical resistant material as the remainder of well walls. In the present embodiment, nine wells are formed as depicted, the right well being separated from the middle well by well wall 2 and the first well being defined by well walls 24, 3, 4, and 1, the second well being defined by well walls 4, 5, 6, and 7, the third well being defined by well walls 7, 8, 9, and 10, the fourth well being defined by well walls 6, 8, 12, and 14, the fifth well being defined by well walls 14, 14, 16, and a front wall, the sixth well being defined by well walls 16, 17, 18 and a rear wall, the seventh well being defined by well walls 18, 19, 20 and 21, the eighth well being defined by well walls 21, 22, 23 and an interior well wall, and the ninth well being defined as the well situated in the center and surrounded by wells 1 through 8, sharing common walls with those wells. It is understood that a greater number of wells than the nine depicted may be juxtaposed together depending on the application. FIG. 4 also depicts a cell or tissue culture 13 situated in the fourth well.

It will be clear to a person skilled in the art that specific embodiments discussed herein are not the only possible modes of this invention that can be manufactured. Many other features that are not shown in the described embodiments are within the scope of this invention.

What is claimed is:

1. A cell or tissue culture assembly for assessing signal communication of physically separated cell or tissue cultures, the cell or tissue culture assembly made of non media-permeable material and having a base and a plurality of separate juxtaposed side-by-side wells having common interior well walls preventing physical contact or movement of chemical factors between the separated cell or tissue cultures, the walls having different heights and defining an outer "surround" cell or tissue culture and one or more inner "center" cell or tissue cultures to enable contained cell or tissue communication between the well spaces, the wells configured to comprise two or more cell or tissue cultures, the wells permitting signal communication between the cells or tissues situated within said wells.

2. The cell or tissue culture assembly of claim 1, further characterized by said wells having interiors which atmospherically communicate with each other.

3. The cell or tissue culture assembly of claim 1 or 2, wherein said wells may be circular, square, rectangular, pentagonal, hexagonal, or a number of additional geometric shapes, either similar to each other in shape or mixed in shape.

4. The cell or tissue culture assembly of claim 1 or 2, manufactured using any dimensionally stable chemical resistant transparent material.

5. The cell or tissue culture assembly of claim 1 or 2, manufactured by using a material selected from the group consisting of glass, acrylic polymers, fluorinated ethylene propylene, ultra high molecular weight polyethylene, polycarbonate, polystyrene, or any amorphous high-performance polymer.

6. The cell or tissue culture assembly of claim 1 or 2, characterized by said base having a plurality of well walls lying in a plane perpendicular to said base, providing a surround well and a plurality of center wells.

7. The cell or tissue culture assembly of claim 6, characterized by said base having identifying numbers indelibly associated with each of said wells.

8. The cell or tissue assembly of claim 1, wherein three cell or tissue culture wells are juxtaposed side-by-side, all said wells having common interior walls.

9. The cell or tissue culture assembly of claim 1, wherein nine cell or tissue culture wells are juxtaposed side-by-side, all said wells having common interior walls.

10. The cell or tissue culture assembly of claim 6, further characterized by said wells having interiors which atmospherically communicate with each other as influenced by the surround and center well wall dimensions.

* * * * *